(12) United States Patent
Lai et al.

(10) Patent No.: US 7,407,285 B2
(45) Date of Patent: Aug. 5, 2008

(54) METHOD AND APPARATUS FOR OBTAINING PATIENT-VERIFIED PRESCRIPTION OF HIGH ORDER ABERRATIONS

(76) Inventors: Ming Lai, P. O. Box 10845, Pleasanton, CA (US) 94588; Casimir Swinger, 304 E. 65th Street, Apt. 30A, New York, NY (US) 10021; Meijuan Yuan, 5615 Cedar Crest Ter., Dublin, CA (US) 94568

( * ) Notice: Subject to any disclaimer, the term of this patent is extended or adjusted under 35 U.S.C. 154(b) by 782 days.

(21) Appl. No.: 10/718,451

(22) Filed: Nov. 19, 2003

(65) Prior Publication Data

US 2004/0160576 A1 Aug. 19, 2004

Related U.S. Application Data

(60) Provisional application No. 60/428,211, filed on Nov. 20, 2002.

(51) Int. Cl.
*A61B 3/10* (2006.01)
(52) U.S. Cl. .................. 351/205; 351/211; 351/216
(58) Field of Classification Search ............. 351/205, 351/212, 216, 222, 233, 237
See application file for complete search history.

(56) References Cited

U.S. PATENT DOCUMENTS

| 5,144,630 | A | 9/1992 | Lin |
|---|---|---|---|
| 5,520,679 | A | 5/1996 | Lin |
| 5,632,742 | A | 5/1997 | Frey et al. |
| 5,645,550 | A | 7/1997 | Hohla |
| 5,777,719 | A | 7/1998 | Williams et al. |
| 5,782,822 | A | 7/1998 | Telfair et al. |
| 5,949,521 | A | 9/1999 | Williams et al. |
| 6,031,854 | A | 2/2000 | Ming |
| 6,688,745 | B2 * | 2/2004 | Ross et al. .............. 351/206 |
| 6,736,507 | B2 * | 5/2004 | Kudryashov et al. ........ 351/206 |
| 2002/0013575 | A1 | 1/2002 | Lai |

FOREIGN PATENT DOCUMENTS

| WO | WO 99/55216 | 11/1999 |
|---|---|---|
| WO | WO 00/04952 | 2/2000 |

* cited by examiner

*Primary Examiner*—Ricky L Mack
*Assistant Examiner*—Brandi N Thomas

(57) ABSTRACT

The present invention contemplates an ophthalmic adaptive-optics instrument to obtain patient-verified prescription of low and high-order aberrations. The present invention further contemplates a new and improved method and apparatus of customized corneal ablation using a patient-verified prescription of low and high-order aberrations. The patient-verified prescription of high-order aberrations characterizes the aberration correction needed for optimal visual acuity and enables customized corneal ablation to achieve optimal visual acuity for each individual patient.

15 Claims, 3 Drawing Sheets

METHOD AND APPARATUS FOR OBTAINING PATIENT-VERIFIED PRESCRIPTION OF HIGH ORDER ABERRATIONS

This application claims the benefit of U.S. Provisional Application No. 60/428,211, filed on Nov. 20, 2002.

FIELD OF THE INVENTION

The present invention relates to a method and apparatus for obtaining a patient-verified prescription of high-order aberrations. In particular, the present invention relates to the method and apparatus for obtaining patient-verified optical prescriptions that include high order aberrations that can be subsequently used for performance of customized corneal ablation in photorefractive surgery.

BACKGROUND OF THE INVENTION

Topography link and/or wavefront guided custom ablation is a newly developed technology aiming to achieve supernormal visual acuity through photorefractive surgery. In a custom-ablation photorefractive surgical procedure, a computer of the surgical system reads in the patient's data from a topography or wavefront device and controls the scan of a surgical laser beam to generate a customized ablation profile on the subject's cornea. It can thus remove corneal irregularity and correct low and high-order optical aberrations of the subject's eye.

It is generally expected that the patient's visual acuity, contrast sensitivity and visual function would be significantly improved once the refractive prescription and any irregularity, or high-order aberrations are removed. These irregularities and high-order aberrations of the subject's eye can be measured objectively by a corneal topographer or ophthalmic wavefront instrument. As the diagnostic instrumentation and the refractive surgery procedures themselves have been refined, however, there has been a controversy with respect to the results that have been observed. It has been found clinically that people with excellent visual acuity, such as jet-fighter pilots, may have high-order aberrations not significantly different from normal eyes, while patients who have undergone a reduction in their high-order aberrations may have similar visual acuity as normal eyes.

It is understood that conventional customized ablation is based on objective diagnostic data of the eye. Conventional customized ablation attempts to make the patient's eye into an aberration-free optical system. On the other hand, visual acuity is rather a subjective phenomenon, involving image recognizing and processing by the human brain. The neurological processes involved in constructing a visual image are expected to vary between individuals. Therefore, an aberration-free eye may not necessarily produce optimal visual acuity and function in a given patient, and it is thereby conceivable that the optimal visual acuity may be attained by an eye not free of aberrations. This has been the clinical experience. It is well known that the lower order aberrations (refractive sphere and cylinder) as determined objectively with instrumentation needs to be refined clinically, using the patient's subjective response, to allow the patient to choose the required optical prescription that satisfies the entire optical system, comprised of the eye and the brain. Any customized refractive surgical procedure that uses objective data without the subjective participation by the patient may thus be less than ideal.

SUMMARY OF THE INVENTION

The present invention recognizes the limitation with conventional custom ablation in photorefractive surgery and contemplates a new and improved method and apparatus for customized corneal ablation using patient-verified prescription of low and high-order aberrations. The present invention further contemplates an ophthalmic adaptive-optics instrument to obtain patient-verified prescriptions of low and high-order aberrations. The subjective patient-verified prescription of high order aberration allows characterization of the requisite aberration correction needed for optimal visual acuity and enables customized corneal ablation to achieve optimal visual acuity for each individual patient.

In one embodiment of the present invention, an ophthalmic adaptive-optics instrument is implemented with an observation target, a deformable mirror, a wavefront sensor, processing electronics, and a subjective feedback control. The instrument enables the patient to look at the observation target via the deformable mirror. The wavefront sensor senses the eye's aberrations also via the deformable mirror. The amount of the aberration compensation imposed by the deformable mirror is adjusted and verified by the patient such that optimal visual acuity can be achieved. The instrument measures the total aberration of the eye and the residual aberration for optimal visual acuity. The instrument can then subtract the residual aberration from the total aberration to provide a patient-verified prescription of low-and high-order aberrations for optimal visual acuity.

Accordingly, an objective of the present invention is to provide a new and improved method and apparatus for customized ablation in photorefractive surgery.

Another objective of the present invention is to provide a new and improved method and apparatus for customized ablation based on patient-verified prescription of low and high-order aberrations.

A further objective of the present invention is to provide a new and improved method and apparatus for obtaining patient-verified prescriptions of low and high-order aberrations.

Another further objective of the present invention is to provide a new and improved method and apparatus employing a deformable mirror/adaptive optics element to obtain patient-verified prescriptions of low and high-order aberrations.

The above and other objectives and advantages of the present invention will become more apparent in the following drawings, detailed description, and claims.

DETAILED DESCRIPTION OF THE DRAWINGS

Figure 1:
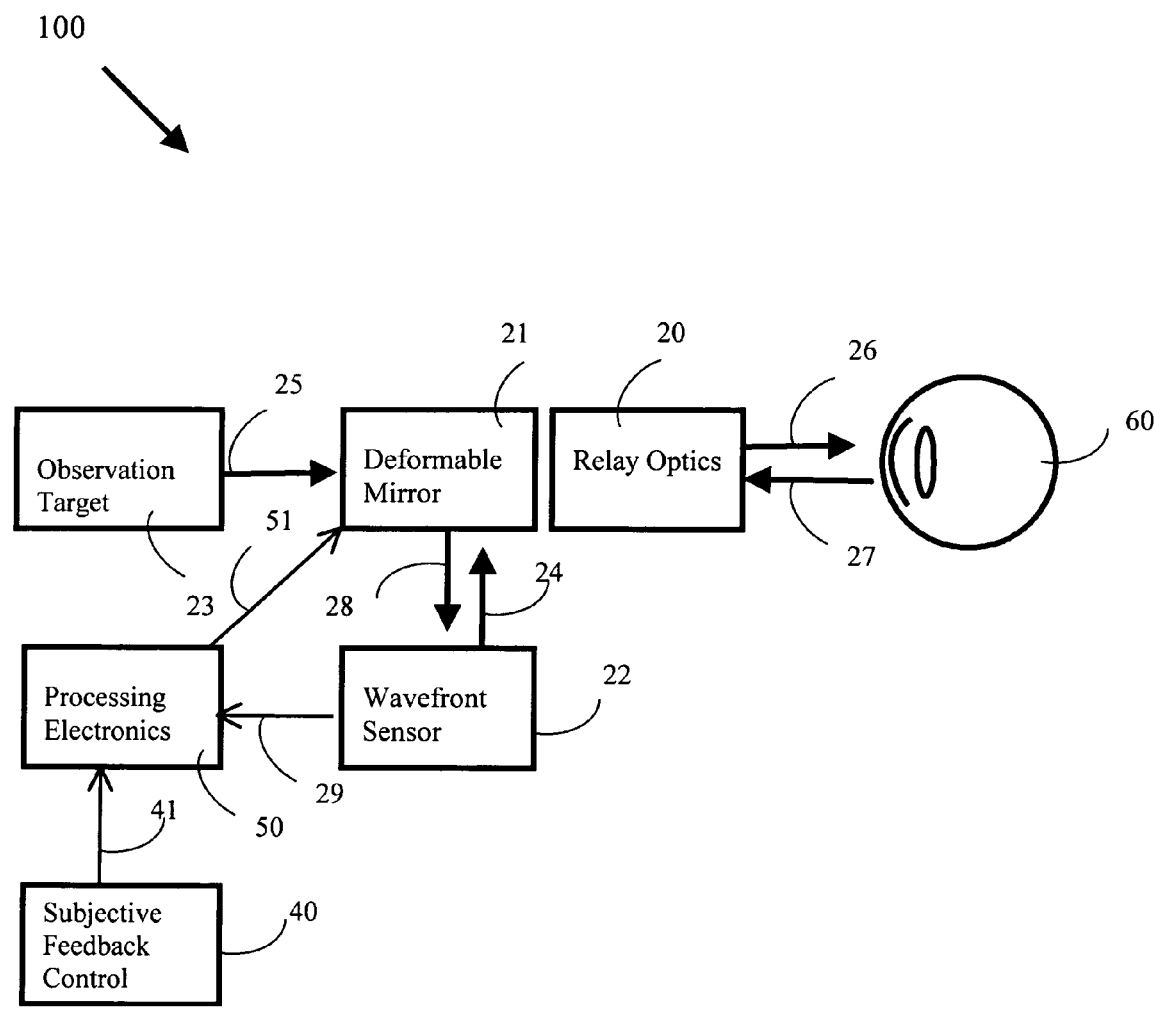
FIG. 1 shows schematically an ophthalmic adaptive-optics instrument for obtaining patient-verified prescription of low- and high-order aberrations.

FIG. 1 shows schematically an ophthalmic adaptive-optics instrument 100 for obtaining patient-verified prescriptions of low-and high-order aberrations, in accordance with the present invention. The ophthalmic adaptive-optics instrument 100 consists of relay optics 20, a deformable mirror 21, a wavefront sensor 22, an observation target 23, a subjective feedback control 40, and a processing electronics 50.

The relay optics 20 relays the wavefront of an outgoing beam 27 from the pupil plane to the deformable mirror 21. The relay optics 20 comprises two or more lenses with all of their own high-order aberrations well balanced and minimized. The relay optics 20 may include a set of compensation lenses or other mechanism to compensate low order aberrations of the subject eye, such as defocusing and regular astigmatism. The construction and alignment of relay optics 20 are known to those skilled in the art.

The deformable mirror 21 is used here as an aberration-compensating element to modify or compensate the wavefront distortion of a light beam impinging on it. The deformable mirror 21 is an adaptive-optics element, and it can produce a position-dependent phase modulation across the beam, according to a programmable control signal 51. Therefore, the deformable mirror 21 works as a spatial phase modulator and can be replaced by other types of spatial phase modulators. The construction and control algorithm of a deformable mirror are known to those skilled in the art.

The wavefront sensor 22 projects a probe beam 24/26 into the subject eye 60 via the deformable mirror 21. The scattered light from the eye's retina forms an outgoing beam 27 from the eye 60. This outgoing beam 27 passes through the deformable mirror 21 and turns into beam 28. The wavefront of the beam 28 is measured with the wavefront sensor 22. The wavefront sensor 22 produces an output signal 29 indicating the aberration of the beam 28. Therefore, the wavefront sensor 22 can measure the total aberration of the eye 60 when the aberration compensation of the deformable mirror 21 is null and the residual aberration of the eye 60 through the deformable mirror 21 with controllable aberration compensation.

The wavefront sensor 22 can be a Hartmann-Shack device or other wavefront sensor such as one operating on the principle of wavefront curvature. The construction and alignment of wavefront sensor 22 are known to those skilled in the art.

The observation target 23 is for the patient to fixate on. It can have an illuminated starburst pattern or other patterns commonly used in ophthalmic instruments. The structure and alignment of observation targets are known to those skilled in the art.

The processing electronics 50 reads in the signal 29 and a command signal 41 and generates a control signal 51 to drive the deformable mirror 21. The deformable mirror 21 thus modifies and compensates the aberration of the subject eye 60 according to the control signal 51.

In an embodiment of the present invention, the amount of aberration compensation of the deformable mirror 21 is controlled by the command signal 41 from the subjective feedback control 40. This feedback control can be operated by a second party, although the determination of optimal image is always made by the patient. The subjective feedback control 40 is adjusted according to the patient's judgment toward an optimal visual acuity.

In measurement, the patient's eye 60 looks at the observation target 23 through the deformable mirror 21 and the patient makes his or her own judgment regarding optimal visual acuity. First, the total aberration of the subject eye 60 is measured and saved as electronic data, while the command signal 41 from the subjective feedback control 40 is set to null. The amount of aberration to be compensated is then adjusted step by step, through the subjective feedback control 40, until an optimal visual acuity is achieved and verified by the patient. If a coma is measured in a subject eye, for example, the compensation on the coma aberration can be made step by step until the subject eye sees an optimal visual acuity. The residual aberration corresponding to the optimal visual acuity is then measured and saved as electronic data.

A patient-verified prescription of low-and high-order aberrations that consider the entire visual system can then be obtained by subtracting the residual aberration from the total aberration of the subject eye 60. The patient-verified prescription carries all the parameters of aberration compensation needed for achieving optimal visual acuity for the subject eye. This patient-verified prescription thus provides the ideal parameters for customized cornea ablation and customized lens making, such as customized contact lens, customized eyeglasses and customized intra-ocular lens.

Figure 2:
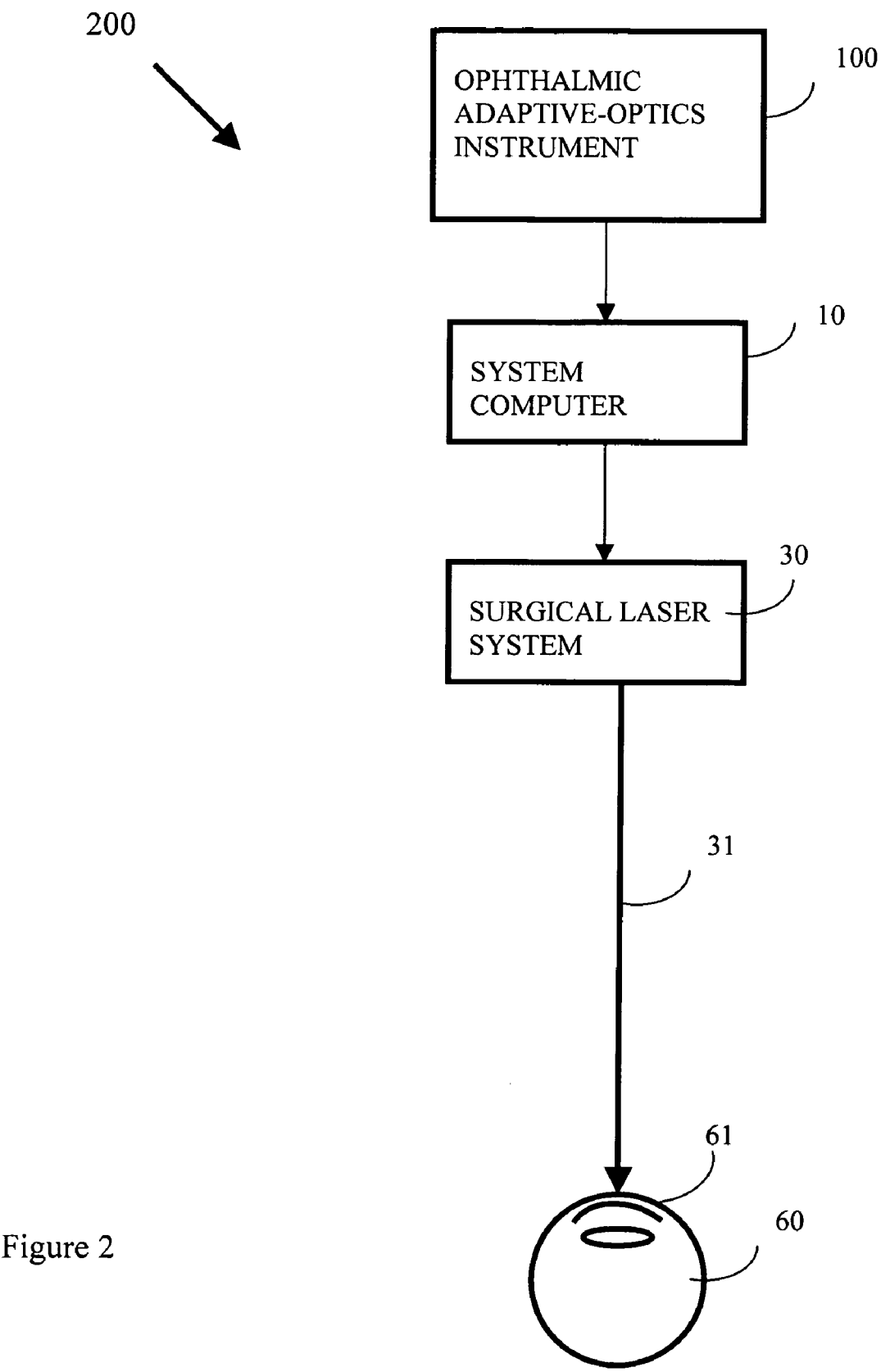
FIG. 2 shows schematically a surgical station for custom cornea ablation using patient-verified prescription of low- and high-order aberrations.

FIG. 2 shows schematically a surgical station 200 for custom corneal ablation using patient-verified prescription of low and high-order aberrations. The surgical station 200 consists of an ophthalmic adaptive-optics instrument 100, a system computer 10, and a surgical laser system 30.

The ophthalmic adaptive-optics instrument 100 can be as described in FIG. 1 and is operationally coupled to the system computer 10. The ophthalmic adaptive-optics instrument 100 provides a patient-verified prescription of low and high-order aberrations and the data of the prescription are saved in electronic format and transformable through electronic means.

The system computer 10 reads in the patient-verified prescription of low and high-order aberrations and generates a data file for customized ablation. This data file is to provide an ablation profile that reduces the eye's aberration to the values where optimal visual acuity shall be achieved according to the patient-verified prescription.

The surgical laser system 30 projects and scans a surgical laser beam 31 onto the cornea 61 of a subject eye 60. The system computer 10 controls the scan of the surgical laser beam 31 to produce a customized ablation profile based on the patient-verified prescription and aimed for an optimal visual acuity.

The laser wavelength and fluence of the surgical laser beam 31 are predetermined and are known to those skilled in the art. For the purpose of customized corneal ablation, the surgical laser beam 31 can be delivered from an excimer laser operated at a wavelength of 193 nm and a pulse rate between 10 to 600 Hz. More preferably, the surgical laser beam 31 is delivered from a solid state UV laser source operated at a wavelength around 210 nm and a pulse rate between 200 to 2000 Hz. The surgical laser beam 31 shall have on the cornea a spot size ranging from 300 to 800 microns. To assure accurate ablation, the surgical system shall equip a fast eye-tracking device to compensate the eye movement during the surgery. The tracking device is preferably operated at a detection rate of 50 to 5000 Hz.

Figure 3:
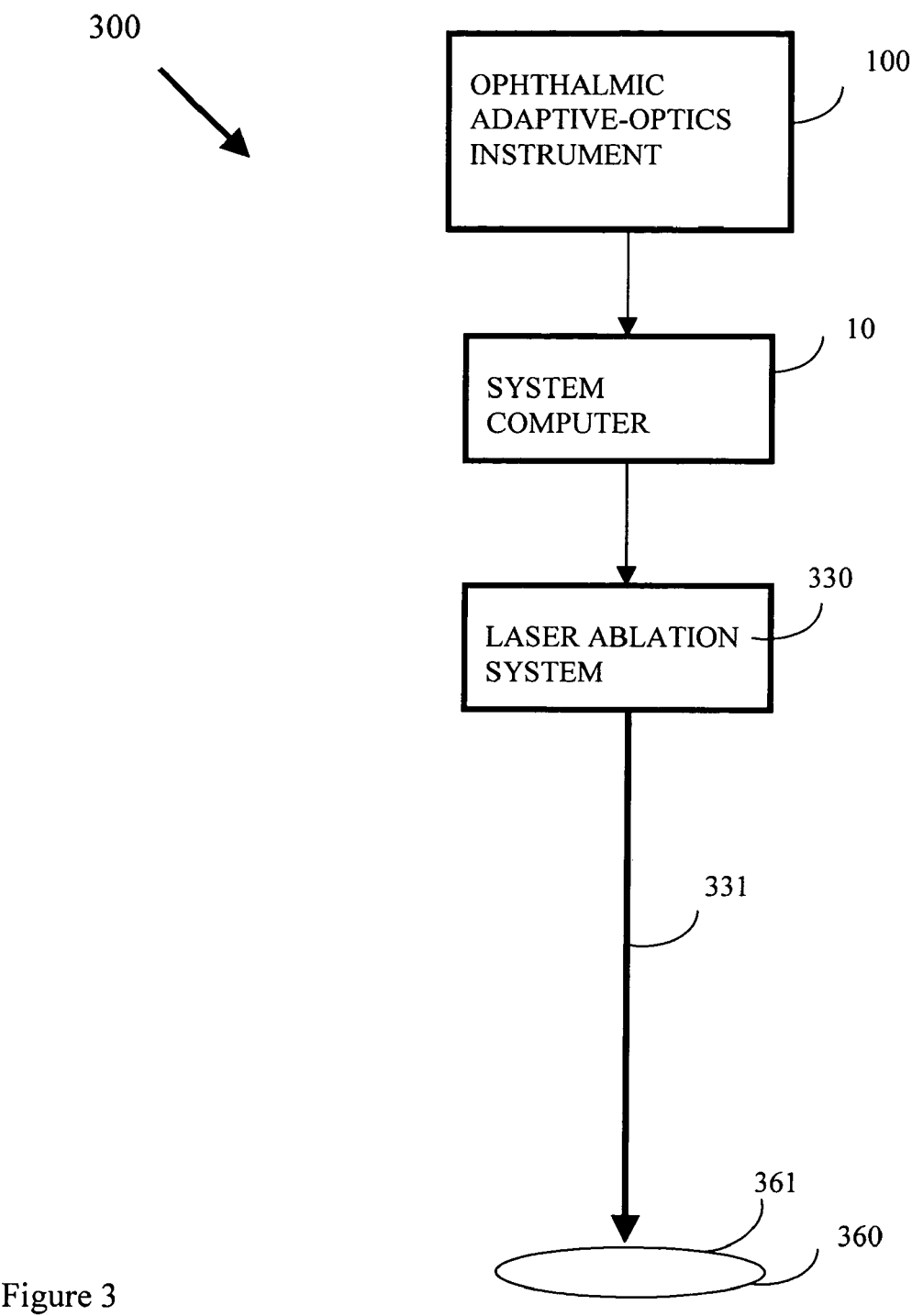
FIG. 3 shows schematically a lens making station for custom optics using patient-verified prescription of low and high-order aberrations.

FIG. 3 shows schematically an embodiment of a lens making station 300 for custom optics using patient-verified prescription of low- and high-order aberrations. The lens making station 300 consists of an ophthalmic adaptive-optics instrument 100, a system computer 10, and a laser ablation system 330. This embodiment of lens making station 300 employs laser ablation to create a custom profile on a surface 361 of a custom lens 360.

The ophthalmic adaptive-optics instrument 100 can be as described in FIG. 1 and is operationally coupled to the system computer 10. The ophthalmic adaptive-optics instrument 100 provides a patient-verified prescription of low- and high-order aberrations and the data of the prescription are saved in electronic format and transformable through electronic means.

The system computer 10 reads in the patient-verified prescription of low-and-high order aberrations and generates a data file for customized ablation of surface 361 of custom lens 360. This data file is to provide an ablation profile that compensates the eye's aberration to the values where optimal visual acuity shall be achieved according to the patient-verified prescription.

The laser ablation system 330 projects and scans an ablation laser beam 331 on surface 361 of the custom lens 360. The system computer 10 controls the scan of the ablation laser beam 331 to produce a customized ablation profile based on the patient-verified prescription and aimed for an optimal visual acuity.

The laser wavelength and fluence of the ablation laser beam 331 are predetermined and are known to those skilled in the art. For the purpose of custom lens ablation, the ablation laser beam 331 can be delivered from an excimer laser operated at a wavelength of 193 nm if the lens material is PMMA. Other laser wavelength may be used for custom lens making according to lens material to be used.

The custom lens 360 can be a contact lens, eyeglasses, or an intra-ocular lens. The embodiment of lens making station 300 employs laser ablation to create a custom profile on a surface 361 of custom lens 360. Lens making station employing other mechanism can also benefit from patient-verified prescription to produce custom lenses for optimal visual acuity.

Although the above description is based on preferred embodiments, various modifications can be made without departing from the scopes of the appended claims.

What is claimed is:

1. An ophthalmic adaptive-optics instrument for obtaining patient-verified prescription of low and high-order aberrations, comprising:
   an observation target disposed for a subject eye to fixate upon;
   an aberration-compensating element disposed in the observation path of said subject eye, wherein said aberration-compensating element is driven by a control signal and is capable of compensating low and high-order aberrations of said subject eye;
   a wavefront-sensing device sensing the aberration of said subject eye via said aberration-compensating element, wherein said wavefront-sensing device measures a residual aberration of said subject eye through said aberration-compensating element with controllable aberration compensation;
   processing electronics coupled to said wavefront-sensing device and accepting a command signal to generate said control signal to drive said aberration-compensating element; and
   subjective feedback control means enabling the patient to actively produce said command signal to adjust said aberration-compensating element and to verify the amount of aberration compensation for optimal visual acuity;
   wherein said ophthalmic adaptive-optics instrument can measure the total aberration of said subject eye, corresponding to a null command signal, and the residual aberration for optimal visual acuity, corresponding to a command signal for optimal visual acuity; and
   wherein said ophthalmic adaptive-optics instrument provides, by subtracting said residual aberration for optimal visual acuity from said total aberration, said patient-verified prescription of low and high-order aberrations.

2. An ophthalmic adaptive-optics instrument of claim 1, wherein said aberration-compensating element is a deformable mirror.

3. An ophthalmic adaptive-optics instrument of claim 1, wherein said aberration-compensating element consists of a deformable mirror and a set of compensation lenses.

4. An ophthalmic adaptive-optics instrument of claim 1, wherein said aberration-compensating element is a spatial phase modulator.

5. An ophthalmic adaptive-optics instrument of claim 1, wherein said wavefront-sensing device is a Hartmann-Shack wavefront sensor.

6. An ophthalmic adaptive-optics instrument of claim 1, wherein said wavefront-sensing device is a curvature wavefront sensor.

7. An ophthalmic adaptive-optics instrument of claim 1, further comprising:
   relay optics relaying wavefront at pupil of said subject eye to said aberration-compensating element.

8. An ophthalmic adaptive-optics instrument of claim 7, wherein said relay optics comprises two or more lenses.

9. An ophthalmic adaptive-optics instrument of claim 7, wherein said relay optics includes a set of compensation lenses to compensate low order aberrations of said subject eye.

10. An ophthalmic adaptive-optics instrument of claim 1, wherein said observation target has an illuminated starburst pattern.

11. An ophthalmic adaptive-optics instrument of claim 1, wherein said subjective feedback control is operated by said patient himself or herself.

12. An ophthalmic adaptive-optics instrument of claim 1, wherein said subjective feedback control is operated by a second party other than said patient.

13. An ophthalmic adaptive-optics instrument of claim 1, wherein data of said patient-verified prescription is saved in electronic format.

14. An ophthalmic adaptive-optics instrument of claim 1, wherein data of said patient-verified prescription is transformable through electronic means.

15. A method for obtaining patient-verified prescriptions of low and high-order aberrations, comprising the steps of:
   providing an observation target for a subject eye to fixate;
   providing an aberration-compensating element disposed in the observation path of said subject eye, wherein said aberration-compensating element is driven by a control signal and is capable to compensate low and high order aberrations of said subject eye;
   providing a wavefront-sensing device to sense the aberration of said subject eye via said aberration-compensating element, wherein said wavefront-sensing device measures a residual aberration of said subject eye through said aberration-compensating element with controllable aberration compensation;
   providing processing electronics coupled to said wavefront-sensing device and read in a command signal;
   generating said control signal to drive said aberration-compensating element;
   providing subjective feedback control means to enable the patient actively to produce said command signal to adjust said aberration-compensating element and to verify the amount of aberration compensation for optimal visual acuity;
   measuring the total aberration of said subject eye, corresponding to a null command signal;
   measuring the residual aberration for optimal visual acuity, corresponding to a command signal for optimal visual acuity; and
   determining said patient-verified prescription of low and high-order aberration by subtracting said residual aberration for optimal visual acuity from said total aberration.

* * * * *